(12) United States Patent
Woods et al.

(10) Patent No.: US 8,759,770 B1
(45) Date of Patent: Jun. 24, 2014

(54) SYSTEM AND METHOD FOR QUALIFYING USABILITY RISK ASSOCIATED WITH SUBSURFACE DEFECTS IN A MULTILAYER COATING

(71) Applicant: General Electric Company, Schenectady, NY (US)

(72) Inventors: Steven Charles Woods, Easley, SC (US); James Carroll Baummer, Greenville, SC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/858,172

(22) Filed: Apr. 8, 2013

(51) Int. Cl.
  *G01J 5/02* (2006.01)
  *G01N 25/00* (2006.01)
  *G01N 21/88* (2006.01)

(52) U.S. Cl.
  CPC ..................................... *G01N 21/88* (2013.01)
  USPC .......... 250/338.1; 374/57; 374/121; 250/330; 382/152

(58) Field of Classification Search
  USPC ................. 250/330, 332, 338.1, 339.04, 342; 374/121, 45, 57; 382/152
  See application file for complete search history.

(56) References Cited

U.S. PATENT DOCUMENTS

| | | | |
|---|---|---|---|
| 3,499,153 A | 3/1970 | Stanfill, III | |
| 5,111,048 A | 5/1992 | Devitt et al. | |
| 6,000,844 A | 12/1999 | Cramer et al. | |
| 6,394,646 B1 | 5/2002 | Ringermacher et al. | |
| 6,838,670 B2 | 1/2005 | Lewis et al. | |
| 6,874,932 B2 * | 4/2005 | Devitt et al. | 374/5 |
| 6,877,894 B2 | 4/2005 | Vona et al. | |
| 7,083,327 B1 | 8/2006 | Shepard | |
| 7,129,492 B2 | 10/2006 | Saito et al. | |
| 7,220,966 B2 | 5/2007 | Saito et al. | |
| 7,388,204 B2 | 6/2008 | Key et al. | |
| 7,409,313 B2 | 8/2008 | Ringermacher et al. | |
| 7,432,505 B2 | 10/2008 | Brummel | |
| 7,689,003 B2 | 3/2010 | Shannon et al. | |
| 8,288,726 B2 | 10/2012 | Weil | |
| 8,300,232 B2 | 10/2012 | Sansom et al. | |
| 2002/0018510 A1 | 2/2002 | Murphy et al. | |
| 2003/0115941 A1 | 6/2003 | Srivastava et al. | |
| 2003/0229458 A1 | 12/2003 | Alfano et al. | |
| 2004/0262521 A1 * | 12/2004 | Devitt et al. | 250/341.1 |
| 2012/0050537 A1 | 3/2012 | Ringermacher et al. | |
| 2012/0101769 A1 * | 4/2012 | Zombo et al. | 702/135 |
| 2012/0186260 A1 | 7/2012 | Dicintio et al. | |
| 2013/0026365 A1 | 1/2013 | Jahnke et al. | |
| 2013/0041614 A1 * | 2/2013 | Shepard et al. | 702/130 |

* cited by examiner

*Primary Examiner* — Mark R Gaworecki (74) *Attorney, Agent, or Firm* — Dority & Manning, PA (57) ABSTRACT

A system for qualifying usability risk associated with subsurface defects in a multilayer coating includes a component having a multilayer coating, an infrared detection device for capturing infrared images of the multilayered coating and a processing unit that is in electronic communication with the infrared detection device where the processing unit generates a subsurface defect map of the multilayer coating based on the infrared images. The system further includes a risk map of the component.

20 Claims, 6 Drawing Sheets

SYSTEM AND METHOD FOR QUALIFYING USABILITY RISK ASSOCIATED WITH SUBSURFACE DEFECTS IN A MULTILAYER COATING

FIELD OF THE INVENTION

The present invention relates to a system and a method for qualifying usability risk associated with subsurface defects in a multilayer coating. In particular, the present invention involves using infrared technology to determine size and location of subsurface defects in a multilayer coating such as a thermal barrier coating to qualify usability risk associated with continued use of the multilayer coating.

BACKGROUND OF THE INVENTION

A combustion section of a gas turbine generally includes a plurality of combustors that are arranged in an annular array around an outer casing such as a compressor discharge casing. Pressurized air flows from a compressor to the compressor discharge casing and is routed to each combustor. Fuel from a fuel nozzle is mixed with the pressurized air in each combustor to form a combustible mixture within a primary combustion zone of the combustor. The combustible mixture is burned to produce hot combustion gases having a high pressure and high velocity. The combustion gases are routed towards an inlet of a turbine of the gas turbine through a hot gas path that is at least partially defined by an annular combustion liner and/or an annular transition duct. The hot gas path extends through the turbine and terminates at an outlet of the turbine.

The constant demand for increased operating temperatures in gas turbine engines has necessitated the development of various coating materials such as ceramics that can be applied to the various hot gas paths components such as the combustion liner, the transition duct and/or turbine nozzles and turbine blades to insulate those components from the heat contained in the combustion gases, thereby extending the life of those components. These coatings are known in the art as thermal barrier coatings (TBC).

A thermal barrier coating typically comprises at least one layer of a refractory or thermally insulating material having a low thermal conductivity such as about 1-3 W/(m)(K). The coating material may be applied by one of known deposition techniques such as a thermal or plasma spray process or a physical vapor deposition process. Typically, a thermal barrier coating is applied in multiple layers. In particular applications, a bond-coat is applied to an inner or hot side surface of the liner or transition duct. The bond-coat provides a layer which adheres well to the underlying alloy and that provides protection against oxidation of the alloy. The refractory or thermal insulation coat is then applied over the bond-coat. Some thermal barrier coatings may also include an intermediate layer or interlayer that is applied over the bond-coat. The interlayer may provide improved adhesion for the final thermal insulating coat.

Despite great care taken during manufacture to ensure adhesion of the thermal insulation coat to the bond-coat, thermal cycling eventually leads to subsurface defects in the thermal barrier coating known as delamination or disbonding. Delamination generally leads to spallation that eventually exposes the underlying alloy to extreme temperatures that may impact the durability of the liner and/or transition duct. As a result, the thermal barrier coating must be inspected for subsurface defects during scheduled maintenance or planned outages of the gas turbine. Typically, the thermal barrier coating is stripped and replaced after a pre-determined number of inspection cycles, in part due to limitations of many current inspection processes.

Removal and reapplication of the thermal barrier coating significantly increases the time required to inspect the hot gas path component and contributes substantially to the overall cost of inspection/repair. Therefore, there is a continued need to provide a non-destructive method for determining size and location of subsurface defects in the thermal barrier coating to qualify the risk associated with continued use of the thermal barrier coating.

BRIEF DESCRIPTION OF THE INVENTION

Aspects and advantages of the invention are set forth below in the following description, or may be obvious from the description, or may be learned through practice of the invention.

One embodiment of the present invention is a system for qualifying usability risk associated with subsurface defects in a multilayer coating. The system includes a component having a multilayer coating, an infrared detection device for capturing infrared images of the multilayered coating, a processing unit in electronic communication with the infrared detection device where the processing unit generates a subsurface defect map of the multilayer coating based on the infrared images. The system further includes a risk map of the component.

Another embodiment of the present invention is a system for qualifying usability risk associated with subsurface defects in a thermal barrier coating of a hot gas path component. The system includes a hot gas path component having a thermal barrier coating, a thermal energy source, an infrared detection device for capturing infrared images of the thermal barrier coating and a processing unit that is in electronic communication with the infrared detection device. The processing unit is configured to generate a subsurface defect map of the thermal barrier coating based on the infrared images. The system further includes a risk map of the hot gas path component and an overlay map comprising of the subsurface defect map and the risk map.

The present invention may also include a method for qualifying usability risks associated with subsurface defects in a thermal barrier coating of a hot gas path component. The method comprises generating a subsurface defect map of the thermal barrier coating, generating a risk map of the hot gas component and superimposing the subsurface defect map over the risk map to determine a risk level of the subsurface defect. The method further includes comparing the subsurface defect to allowable inspection limits and qualifying usability risks associated with continued use of the thermal barrier coating based on the comparison to the allowable inspection limits.

Those of ordinary skill in the art will better appreciate the features and aspects of such embodiments, and others, upon review of the specification.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

DETAILED DESCRIPTION OF THE INVENTION

Reference will now be made in detail to present embodiments of the invention, one or more examples of which are illustrated in the accompanying drawings. The detailed description uses numerical and letter designations to refer to features in the drawings. Like or similar designations in the drawings and description have been used to refer to like or similar parts of the invention. As used herein, the term "radially" refers to the relative direction that is substantially perpendicular to an axial centerline of a particular component, and the term "axially" refers to the relative direction that is substantially parallel to an axial centerline of a particular component.

Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents. Although exemplary embodiments of the present invention will be described generally in the context of a thermal barrier coating disposed on a combustion liner and/or a transition duct for a gas turbine for purposes of illustration, one of ordinary skill in the art will readily appreciate that embodiments of the present invention may be applied to any component having a multi-layered thermal coating such as the thermal barrier coating that comes into contact with combustion gases.

Figure 1:
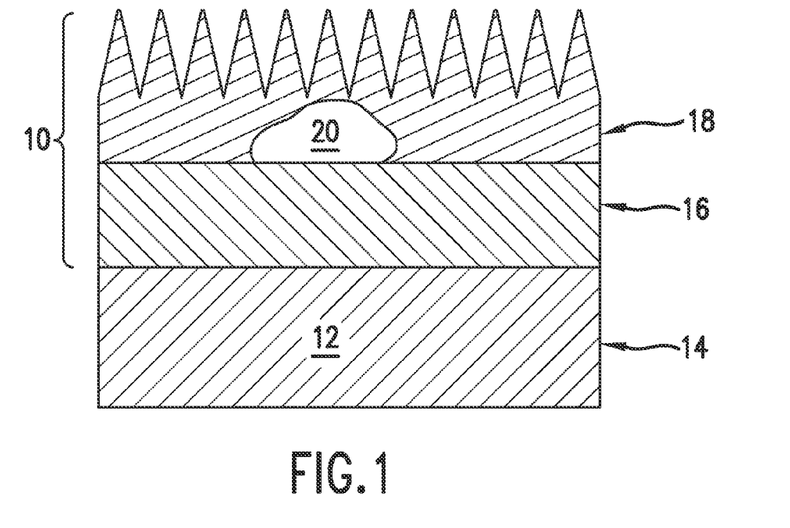
FIG. 1 provides a cross section side view of a typical thermal barrier coating within the scope of the present disclosure.

Referring now to the drawings, wherein identical numerals indicate the same elements throughout the figures, FIG. 1 illustrates a cross section side view of a typical multilayer coating such as a thermal barrier coating 10 herein referred to as "TBC 10". As shown in FIG. 1, the TBC 10 may be disposed on a base metal 12 of a hot gas path component 14 of a gas turbine such as a combustion liner or a transition duct. Although the multilayer coating in the present invention is described as a thermal barrier coating (TBC), it should be obvious to one of ordinary skill in the art that the invention as described herein may be applied to any multilayer coating. As shown in FIG. 1, the TBC 10 is generally applied in multiple layers. A first layer or bond-coat 16 is applied directly to the base metal 12. A second layer or thermal insulation coat 18 is disposed over the bond-coat 16. A typical bond-coat 16 is composed of a metallic material such as nickel or cobalt that is suitable for adhesion to the base metal 12. A typical thermal insulation coat 18 is composed of yttria-stabilized zirconia which is known in the art for having low thermal conductivity while remaining stable at nominal operating temperatures of the gas turbine.

As the hot gas path component 14 cycles through various thermal transients such as during start-up and shut-down of the gas turbine the thermal insulation coat 18 will tend to disbond or delaminate from the bond-coat 14, thereby creating a subsurface defect 20 in the TBC 10. The subsurface defect 20 may result in spallation of the thermal insulation coat 18, thereby compromising the effectiveness of the TBC 10 and/or limiting the durability of the hot gas path component 14. The subsurface defect 20 is generally difficult to detect without stripping the thermal insulation coating 20 from the hot gas path component 14.

Figure 2:
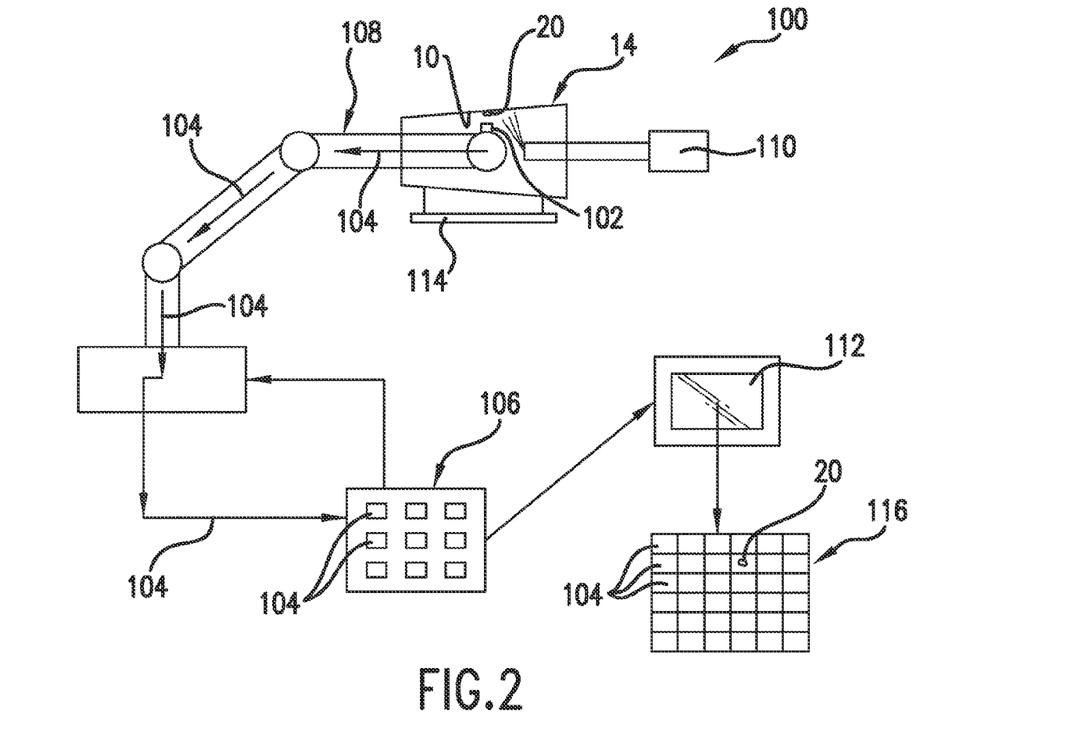
FIG. 2 provides a schematic diagram of a system for qualifying usability risk associated with subsurface defects in a thermal barrier coating according to one embodiment of the present disclosure.

FIG. 2 provides a perspective view of a system 100 for qualifying usability risk associated with continued use of the TBC 10 with the subsurface defect 20 in the TBC 10, herein referred to as the "system 100". As used herein, the term "usability risk" includes risks associated with spallation and/or failure of the TBC 10 which may result in damage to and/or failure of the hot gas component 14. As shown, the system 100 includes an infrared detection device 102 for providing infrared images 104 of the thermal barrier coating 10 to a processing unit 106. The processing unit 106 is in electronic communication with the infrared detection device 102. In one embodiment, the infrared detection device 102 is coupled to an actuatable mechanism 108 such as a robotic arm that manipulates the infrared detection device 102 in at least one of an axial, radial or tangential direction to capture multiple infrared images 104 of the TBC 10 across multiple locations of the hot gas path component 14.

In one embodiment, the system 100 includes a thermal energy source 110 such as a flash lamp or a laser for transferring thermal energy to the TBC 10 and/or the hot gas path component 14. The system 100 may further include a display 112 such as a CRT, LCD or plasma monitor that is electronically connected to the processing unit 106 for displaying the infrared images 104 and/or other information. In particular embodiments, the system 100 further includes a fixture 114 to support the hot gas path component 14 during inspection.

The infrared detection device 102 may include any imaging device such as an infrared camera that is capable of capturing the infrared images 104 of the TBC 10 and electronically transferring the infrared images 104 to the processing unit 106. The processing unit 106 comprises hardware circuitry and software that enables the processing unit 106 to process the infrared images 104 and detect the subsurface defect 20 without removing the thermal insulation coat 18. For example, the processing unit 106 may be configured and/or programmed to analyze the infrared images 104 to measure various infrared wavelengths and/or changes in infrared wavelengths with respect to time to determine the presence of and the length, width and location of the subsurface defect 20 on the hot gas path component 14. In particular embodiments, the processing unit 106 is configured and/or programmed to stitch a plurality of the infrared images 104 together to generate a continuous two dimensional (2-D) subsurface defect map 116 of the hot gas component 14. The subsurface defect map 116 provides location and size of the subsurface defect 20 on a 2-D image of the particular hot gas path component 14. As appreciated by those skilled in the art, the processing unit 106 may include a range of circuitry types, such as a microprocessor, a programmable logic controller, a logic module, etc.

Figure 3:
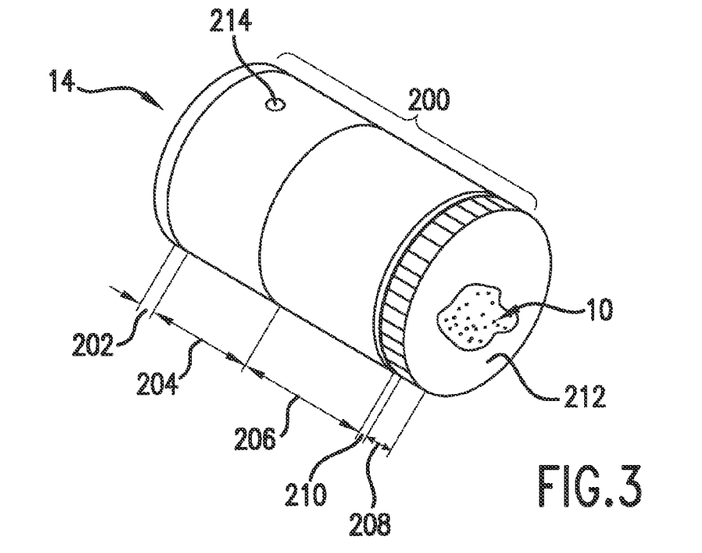
FIG. 3 provides a perspective view of a combustion liner as may be incorporated into one or more embodiments of the present disclosure.

FIG. 3 provides a perspective view of an exemplary hot gas path component 14 as may be incorporated within the scope of this disclosure. As shown, the hot gas path component 14 may comprise an annular combustion liner 200. The combustion liner 200 generally includes a forward portion 202, a combustion portion 204 downstream from the forward portion 202, a gas path portion 206 that extends downstream from the combustion portion 204, an aft portion 208 downstream from the gas path portion 206 and a weld line portion 210 that extends between the gas path portion 206 and the aft end portion 208. An inner surface 212 of the combustion liner 200 is coated with the TBC 10 to protect the base metal of the combustion liner 200 from high temperature combustion gases. The combustion portion 204 may also include various openings 214 for inserting components such as a spark igniter, a cross-fire tube or a flame detector into the combustion liner 200.

Figure 4:
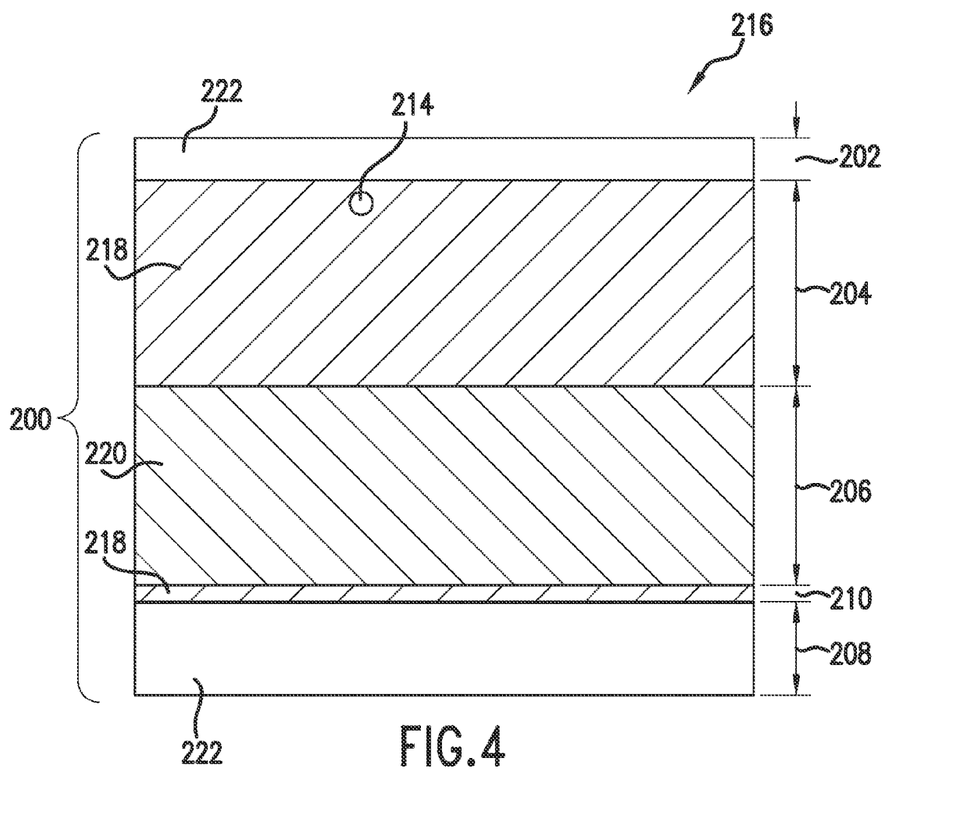
FIG. 4 provides an exemplary risk map of the combustion liner as shown in FIG. 3, according to one embodiment of the present disclosure.

In particular embodiments, as shown in FIG. 4 the system 100 further includes a risk map 216. The risk map 216 is a two dimensional (2-D) map of the hot gas path component 14 that identifies areas of high risk 218, medium risk 220 and low risk 222 associated with continued use the TBC 10 with a known subsurface defect 20. The risk map 216 may comprise of a printed image that is used in conjunction with the subsurface defect map 116 (FIG. 2) that is generated by the processing unit 106. The subsurface defect map 116 may be positioned on top of the risk map 216 to determine the location of the defect 20 and the risk level associated with the defect 20 given its location on the risk map 216.

In one embodiment, the processing unit 106 is configured and/or programmed to generate the two dimensional (2-D) risk map of the particular hot gas path component 14. For example, FIG. 4 represents an exemplary risk map 216 of the combustion liner 200 as shown in FIG. 3, according to one embodiment of the present invention. In particular embodiments, the processing unit 106 is configured and/or programmed to generate the risk map 216 based at least one of the following: stress-strain data, creep data, thermal/mechanical fatigue data, temperature profile data, TBC thermal/mechanical properties, base metal thermal/mechanical properties or bond-coat properties of the particular hot gas path component 14, any or all of which may be based on empirical data such as field reports and/or inspection reports for the particular hot gas component 14, hand calculations and/or finite element analysis of the particular hot gas path component 14.

As shown, the risk map 216 identifies areas of high risk 218, medium risk 220 and low risk 222 with regards to location on the particular hot gas path component 14. The risk level is generally based on susceptibility to thermal/mechanical damage to the base metal of the hot gas path component 12 due to failure or a compromised condition of the TBC 10. For example, as shown in FIG. 4, areas of high risk 218 on the combustion liner 200 are identified at the combustion portion 204 and at the weld line 210, an area of medium risk 220 is identified at the hot gas portion 206 and areas of low risk 222 are identified at the forward portion and aft portion 202, 208 of the combustion liner 200.

Figure 5:
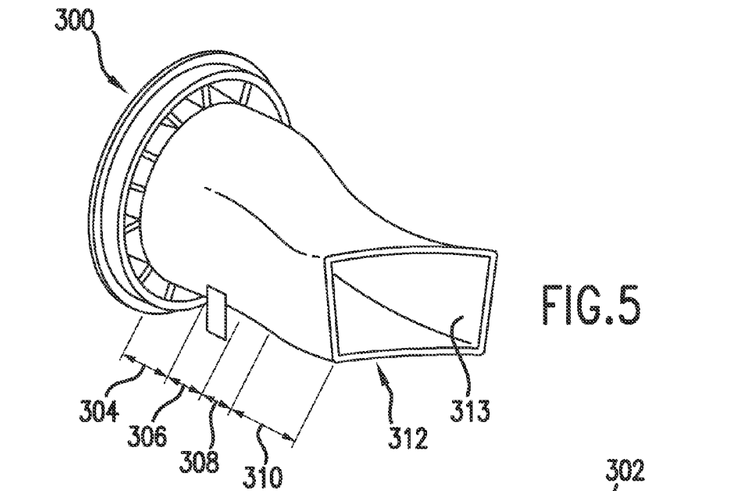
FIG. 5 provides a perspective view of a transition duct as may be incorporated into one or more embodiments of the present disclosure.
Figure 6:
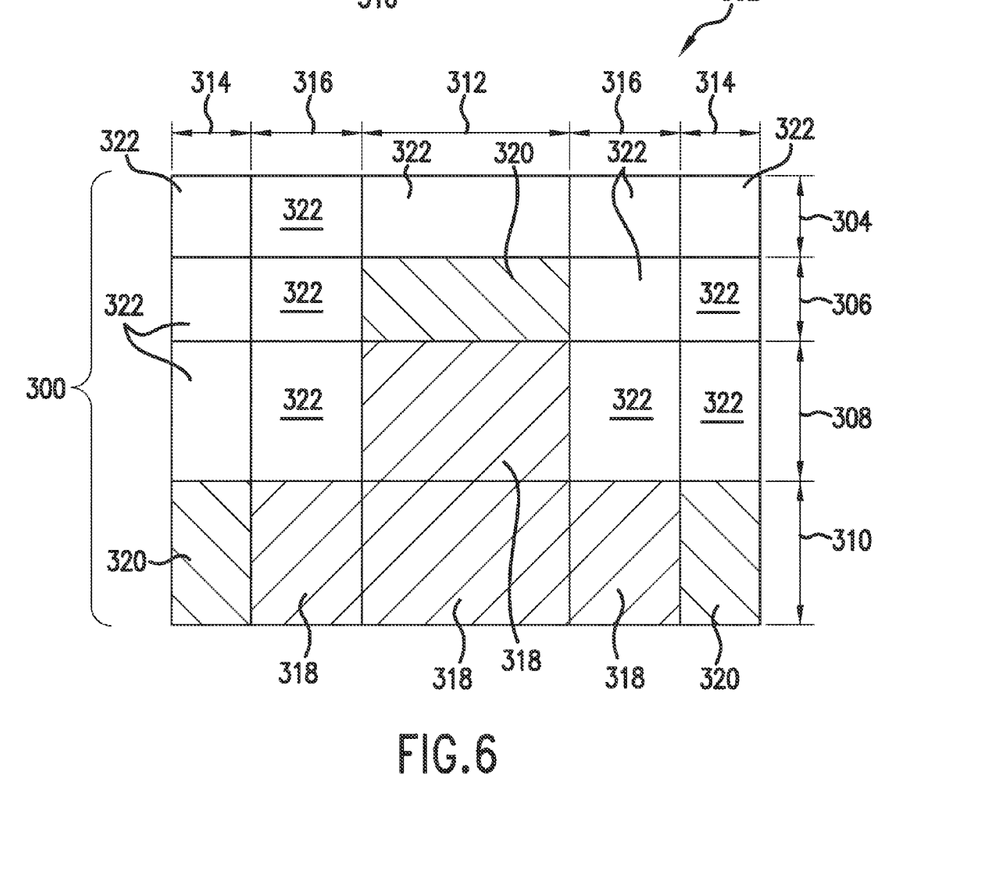
FIG. 6 provides an exemplary risk map of the transition duct as shown in FIG. 5, according to one embodiment of the present disclosure.

In other embodiments, the hot gas path component 14 may comprise a transition duct. FIG. 5 provides a perspective view of an exemplary transition duct 300 of a gas turbine according to one embodiment of the present invention, and FIG. 6 provides a corresponding exemplary risk map 302 for the transition duct 300 according to one embodiment. As shown in FIG. 5, the transition duct 300 generally includes a forward portion 304, a mounting portion 306 that corresponds to an area where the transition duct is mounted to the gas turbine, a generally conical portion 308 and a transition portion 310 which corresponds to a portion of the transition duct 300 where the transition duct transitions to a non-circular cross section. Because the transition duct 300 is not completely conical or circular, the risk map 302 may be further divided to represent a bottom portion 312, a top portion 314 and a pair of opposing side wall portions 316 of the transition duct 300.

For example, as shown in FIG. 6, the risk map 302 may identify areas of high risk 318 at the conical portion 308 along the bottom portion 312 and at the transition portion 310 along the bottom portion 312 and along the pair of opposing side portions 316 of the transition duct 300. Areas of medium risk 320 are identified at the mounting portion 306 along the bottom portion 312 and at the transition portion 310 along the top portion 314 of the transition duct 300. Areas of low risk 322 are identified at the forward end portion 304, at the mounting portion 306 along the top and pair of opposing side portions 314, 316, and at the conical portion 308 along the top and pair of opposing side portions 314, 316.

Figure 7:
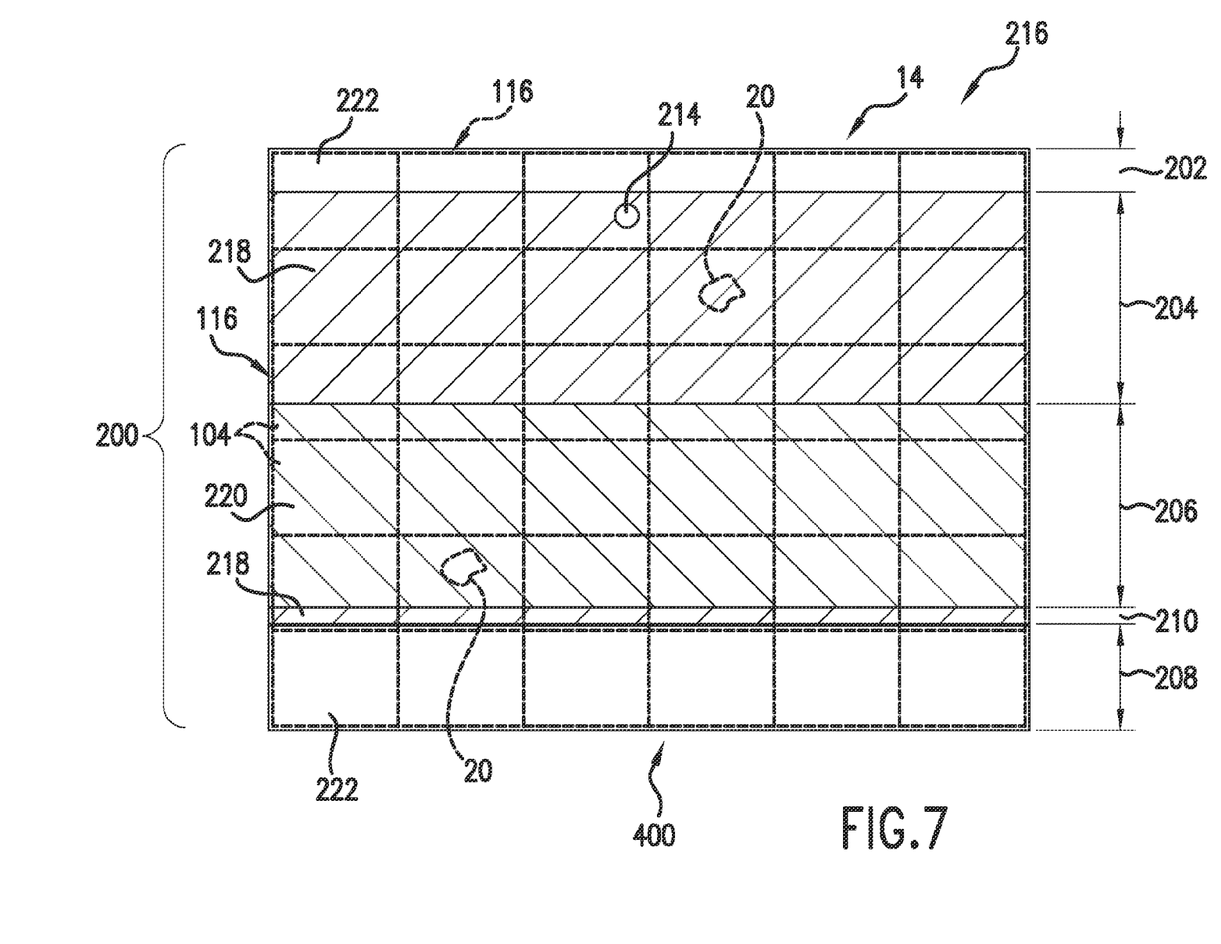
FIG. 7 provides an exemplary overlay map including the risk map as shown in FIG. 4, according to one embodiment of the present disclosure.
Figure 8:
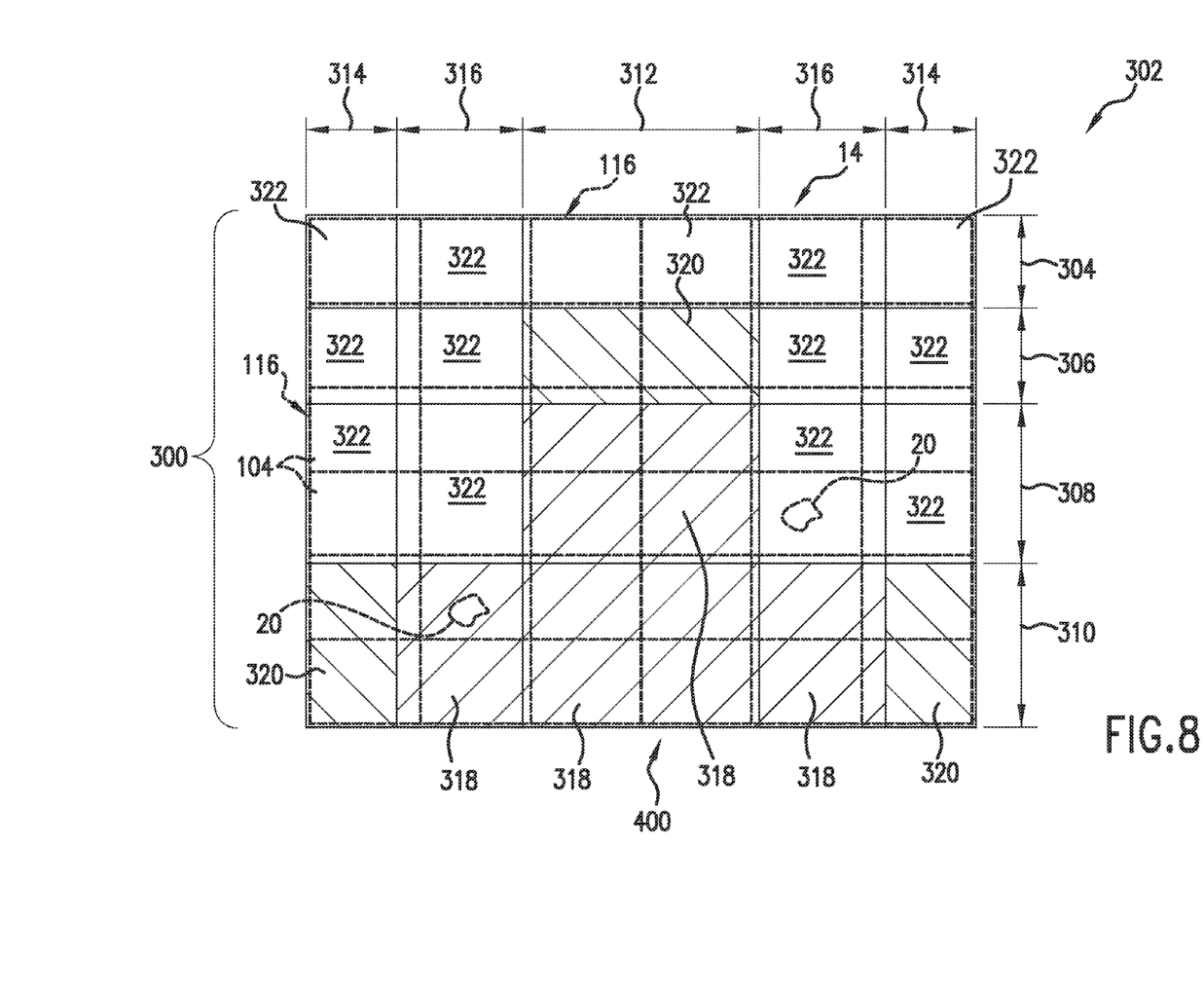
FIG. 8 provides an exemplary overlay map including the risk map as shown in FIG. 6 according to one embodiment of the present disclosure.

As illustrated in FIGS. 7 and 8, the processing unit 106 may be configured and/or programmed to generate an overlay map 400 which graphically superimposes the subsurface defect map 116 over the risk map 216, 302 as illustrated in FIGS. 7 and 8. The overlay map 400 may provide zoomed in images of the subsurface defect 20, dimensions of the subsurface defect 20 and/or location dimensions of the subsurface defect 20 on the hot gas path component 14.

During inspection of the hot gas path component 14 such as the combustion liner 200 or the transition duct 300, the hot gas path component 14 is secured to the fixture 114. Thermal energy may be applied to the TBC 10 and/or to the hot gas component 14 using the thermal energy source 110. The infrared detection device 102 captures the infrared images 104 of the TBC 10 over a period of time as the thermal energy dissipates from the TBC 10. The actuatable mechanism 108 may be used to translate the infrared imaging device 102 to capture infrared images 104 of any portion of hot gas path component 14 having TBC 10.

The processing unit 106 analyzes the infrared images 104 using the hardware and/or software that is designed to detect the subsurface defects 20 in the TBC 10 without removing the thermal insulation coat 18. The processing unit 106 may then stitch the infrared images 104 together to generate the subsurface defect map 116 of the hot gas path component 14. The processing unit 106 and/or a technician may generate an overlay map 400 by superimposing the subsurface defect map 116 over the risk map 216, 302 to determine whether the subsurface defect 20 falls within a high risk location 218, 318 a medium risk location 220, 320 or a low risk location 222, 322 on the hot gas path component 14. For example, as shown in FIG. 7, one subsurface defect 20 is identified within the combustion portion 204, and another subsurface defect is identified within the hot gas portion 206 of the combustion liner 200. As another example, as shown in FIG. 8, one subsurface defect 20 is identified within the transition portion 310 along one of the pair of opposing side portions 316, and a second subsurface defect 20 is identified within the conical portion 308 along one of the opposing side portions 316.

The processing unit 106 is configured and/or programmed to compare the size and/or the location of the subsurface defect 20 to one or more allowable inspection limits that are inputted and/or stored in the processing unit 106 for the particular hot gas path component 14. The allowable inspection limits may be based on one or more of part history, prior subsurface defect maps, operating environment of the hot gas component 14, prior visual inspection data that has been inputted into the processing unit 106, customer provided limit requirements, TBC life curves, TBC composition, base metal composition, empirical damage information, bond-coat composition and/or calculated or empirical stress-strain levels and creep levels. The processing unit 106 is configured and/or programmed to compare the subsurface defects 20 to the allowable inspection limits to generate a pass/fail or go/no-go report for the hot gas path component 14.

Figure 9:
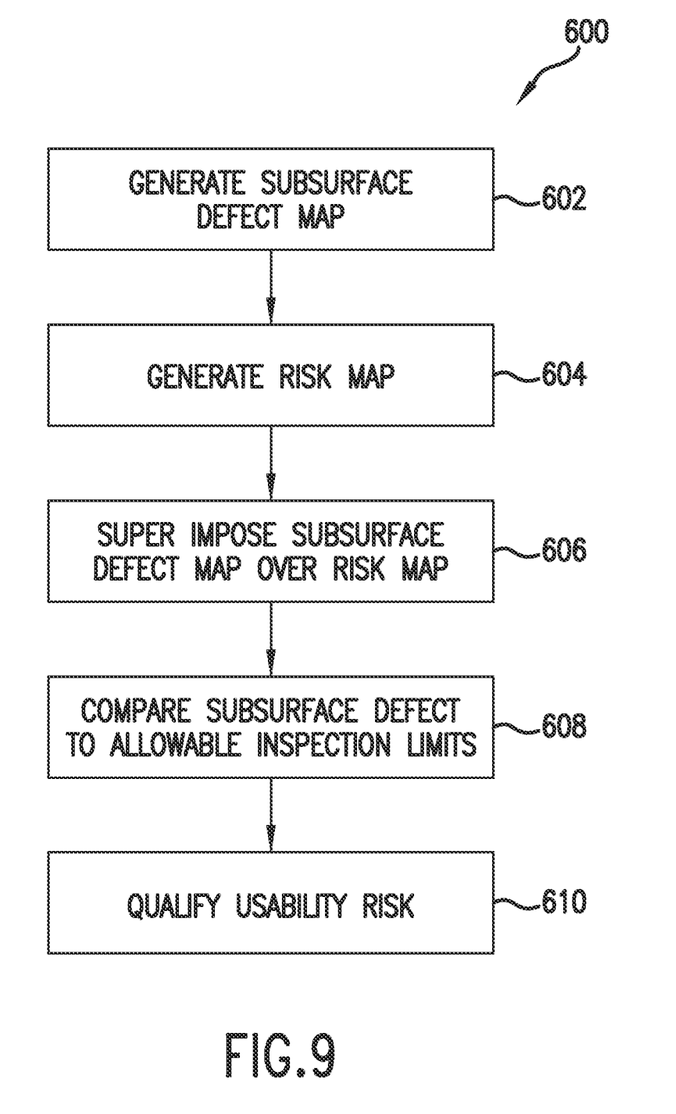
FIG. 9 provides a flow chart representing a method for qualifying usability risk associated with subsurface defects in a thermal barrier coating.

The various embodiments of the system 100 as described herein and as illustrated in FIGS. 2 through 8 provides a method 600 for qualifying usability risk associated with subsurface defects 20 in the TBC 10 disposed on the hot gas path component 14 such as the combustion liner 200 and/or the transition duct 300. As shown in FIG. 9, method 600 includes at step 602 generating the subsurface defect map 116 of the TBC 10 disposed on the hot gas path component 14. Step 602 may be performed using the infrared detection device 102 and the processing unit 106. Step 602 may further include transferring energy such as thermal or ultrasonic energy to at least one of the TBC 10 or the hot gas path component 14, capturing a plurality of time lapse infrared images 104 of the TBC 10 using the infrared imaging device 102, transferring the infrared images 104 to the processing unit 106, and stitching the plurality of infrared images 104 together to provide the continuous subsurface defect map 116. At step 604 the method 600 includes generating the risk map 216, 302 of the hot gas component 14. The risk map 216, 302 may be generated using the processing unit 106 or the risk map 216, 302 may be provided as a printed image. Step 604 may further include inputting into the processing unit 106 at least one of stress-strain data, creep data, thermal fatigue data, mechanical fatigue data, temperature profile data or base metal properties of the hot gas path component.

At 606 the method 600 includes superimposing the subsurface defect map 116 over the risk map 216, 302 to determine the risk level of the subsurface defect 20 based on the location of the subsurface defect 20 on the risk map 216, 302. Step 606 may also be performed using the processing unit 106.

At step 608 the method 600 further includes comparing the subsurface defect 20 to the allowable inspection limits defined at the subsurface defect 20 location on the risk map 216, 302. Step 608 may be performed using the processing unit 106. Step 608 may further include inputting into the processing unit 106 at least one of part history, prior subsurface defect maps, operating environment of the hot gas component, prior visual inspection data, customer provided limit requirements, thermal barrier coating life curves, thermal barrier coating composition, base metal composition, empirical damage information, stress-strain levels or creep levels.

At step 610, the method 600 includes qualifying the usability risk associated with continued use of the thermal barrier coating. Step 610 may be performed using the information contained in the subsurface defect map 116, the risk map 216, 302 and/or the inspection limits. Step 610 may be performed using the processing unit 106. Step 610 may include using the processing unit to generate a pass/fail report based on the inspection limits. The method 600 may further include translating the infrared imaging device 102 using the actuatable mechanism 108 to capture a plurality of infrared images 104 of the TBC 10, and using the processing unit 106 to stitch the plurality of infrared images 104 to form the continuous subsurface defect map 116.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

What is claimed is:

1. A system for qualifying usability risk associated with subsurface defects in a multilayer coating, comprising:
   a component having a multi layer coating;
   an infrared detection device for capturing infrared images of the multilayered coating;
   a processing unit in electronic communication with the infrared detection device, wherein the processing unit generates a subsurface defect map of the multilayer coating based on the infrared images; and
   a risk map of the component.

2. The system as in claim 1, wherein the multilayer coating comprises a thermal barrier coating.

3. The system as in claim 2, further comprising an overlay map that provides a graphical display of the subsurface defect map superimposed onto the risk map.

4. The system as in claim 2, wherein the processing unit generates a pass/fail report for the thermal barrier coating.

5. The system as in claim 2, wherein component is one of a combustion liner or a transition duct.

6. The system as in claim 2, further comprising a thermal energy source for transferring thermal energy to the thermal barrier coating.

7. The system as in claim 2, wherein the thermal barrier coating includes a bond-coat disposed on the hot gas path component and a thermal insulation coat that covers the bond-coat, wherein the subsurface defect map defines at least one of size or location of a subsurface defect between the bond-coat and the thermal insulation coat.

8. The system as in claim 2, wherein the processing unit compares at least one of size or location of the subsurface defect to allowable inspection limits to generate a pass/fail report.

9. The system as in claim 8, wherein the allowable inspection limits are based on at least one of part history, prior subsurface defect maps, operating environment of the hot gas component, prior visual inspection data, customer provided limit requirements, thermal barrier coating life curves, base metal composition, empirical damage information, stress-strain levels or creep levels.

10. A system for qualifying usability risk, associated with subsurface defects in a thermal barrier coating, comprising:
    a hot gas path component having a thermal barrier coating;
    a thermal energy source;
    an infrared detection device for capturing infrared images of the thermal barrier coating;
    a processing unit in electronic communication with the infrared detection. device, wherein the processing unit generates a subsurface defect map of the thermal barrier coating based on the infrared images;
    a risk map of the hot gas path component; and
    an overlay map comprising of the subsurface defect map and the risk map.

11. The system as in claim 10, wherein the overlay map provides a graphical display of the subsurface defect map superimposed onto the risk map.

12. The system as in claim 10, wherein the processing unit compares at least one of size or location of the subsurface defect to allowable inspection limits to generate a pass/fail report.

13. The system as in claim 10, wherein the thermal barrier coating includes a bond-coat disposed on the hot gas path component and a thermal insulation coat that covers the bond-coat, wherein the subsurface defect map identifies at least one of size or location of a subsurface detect between the bond-coat and the thermal insulation coat.

14. The system as in claim 10, further comprising allowable inspection limits that are provided to the processing unit, wherein the allowable inspection limits are based on at least one of part history, prior subsurface defect maps, operating environment of the hot gas component, prior visual inspection data, customer provided limit requirements, thermal barrier coating life curves, base metal composition, empirical damage information, stress-strain levels or creep levels.

15. The system as in claim 10, further comprising an actuatable mechanism coupled to the infrared detection device for translating the infrared detection device across a surface of the hot gas path component, wherein the surface is at least partially covered by the thermal barrier coating.

16. A method for qualifying usability risk associated with subsurface defects in a thermal barrier coating, the method comprising:
    generating a subsurface defect map of the thermal barrier coating;
    generating a risk map of a hot gas component;
    superimposing the subsurface defect map over the risk map to determine a risk level of a subsurface defect defined within the thermal barrier coating;
    comparing the subsurface defect to allowable inspection limits; and
    qualifying usability risk associated with continued use of the thermal barrier coating based on the comparison to the allowable inspection limits.

17. The method as in claim 16, further comprising generating a pass/fail report based on the risk level and the allowable inspection limits.

18. The method as in claim 16, wherein the steps of generating a subsurface defect map, generating a risk map, superimposing the subsurface defect map over the risk map and comparing the subsurface defect to allowable inspection limits are performed using a processing unit.

19. The method as in claim 16, wherein the step of comparing the subsurface defect to allowable inspection limits includes inputting into a processing unit at least one of part history, prior subsurface defect maps, operating environment of the hot gas component, prior visual inspection data, customer provided limit requirements, thermal barrier coating life curves, thermal barrier coating composition, base metal composition, empirical damage information, stress-strain levels or creep levels.

20. The method as in claim 16, wherein the step of generating a subsurface defect map comprises:
    transferring thermal energy to at least one of the thermal barrier coating or the hot gas path component;
    capturing a plurality of time lapse infrared images of the thermal barrier coating using the infrared imaging device; and
    transferring the infrared images to a processing unit.

* * * * *